United States Patent
Watanabe

(10) Patent No.: US 11,678,869 B2
(45) Date of Patent: Jun. 20, 2023

(54) BIOPSY SUPPORT DEVICE, ENDOSCOPE DEVICE, BIOPSY SUPPORT METHOD, AND BIOPSY SUPPORT PROGRAM

(71) Applicant: FUJIFILM Corporation, Tokyo (JP)

(72) Inventor: Hiroki Watanabe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 184 days.

(21) Appl. No.: 16/824,645

(22) Filed: Mar. 19, 2020

(65) Prior Publication Data

US 2020/0268364 A1 Aug. 27, 2020

Related U.S. Application Data

(63) Continuation of application No. PCT/JP2018/040541, filed on Oct. 31, 2018.

(30) Foreign Application Priority Data

Nov. 1, 2017 (JP) .............................. JP2017-212172

(51) Int. Cl.
*A61B 1/00* (2006.01)
*A61B 1/018* (2006.01)
*A61B 10/04* (2006.01)

(52) U.S. Cl.
CPC .......... *A61B 10/04* (2013.01); *A61B 1/00016* (2013.01); *A61B 1/00045* (2013.01); *A61B 1/000094* (2022.02); *A61B 1/018* (2013.01)

(58) Field of Classification Search
None
See application file for complete search history.

(56) References Cited

U.S. PATENT DOCUMENTS

| | | | |
|---|---|---|---|
| 2007/0198194 A1* | 8/2007 | Chait | G01N 33/6848 |
| | | | 702/19 |
| 2007/0213632 A1 | 9/2007 | Okazaki et al. | |
| 2013/0116508 A1 | 5/2013 | Shida | |
| 2014/0221822 A1* | 8/2014 | Ehlers | A61B 5/061 |
| | | | 600/424 |

FOREIGN PATENT DOCUMENTS

| | | |
|---|---|---|
| JP | H08336497 | 12/1996 |
| JP | 2001095749 | 4/2001 |
| JP | 2006230490 | 9/2006 |

(Continued)

OTHER PUBLICATIONS

English Translation of JP Atsushi (JP2001095749A) Apr. 10, 2001.*

(Continued)

*Primary Examiner* — Michael J Carey
*Assistant Examiner* — Minqiao Huang
(74) *Attorney, Agent, or Firm* — JCIPRNET

(57) ABSTRACT

A biopsy support device that supports an inspection using a living tissue sampled by a sampling instrument which is used by being inserted into an endoscope having an imaging element, the biopsy support device including a processor configured to recognize that the living tissue has been sampled by the sampling instrument on the basis of captured image data obtained by capturing an image using the imaging element; and generate identification information corresponding to the living tissue in a case where the living tissue is recognized to have been sampled.

16 Claims, 11 Drawing Sheets

(56) References Cited

FOREIGN PATENT DOCUMENTS

JP     2012010862    1/2012
WO     2006038634    4/2006

OTHER PUBLICATIONS

"Office Action of Japan Counterpart Application" with English translation thereof, dated Apr. 13, 2021, p. 1-p. 10.
"International Search Report (Form PCT/ISA/210)" of PCT/JP2018/040541, dated Jan. 15, 2019, with English translation thereof, pp. 1-3.
"Written Opinion of the International Searching Authority (Form PCT/ISA/237)" of PCT/JP2018/040541, dated Jan. 15, 2019, with English translation thereof, pp. 1-17.
"Office Action of Japan Counterpart Application" with English translation thereof, dated Oct. 5, 2021, p. 1-p. 6.
"Office Action of Japan Counterpart Application" with English translation thereof, dated Apr. 19, 2022, p. 1-p. 5.

* cited by examiner

BIOPSY SUPPORT DEVICE, ENDOSCOPE DEVICE, BIOPSY SUPPORT METHOD, AND BIOPSY SUPPORT PROGRAM

CROSS-REFERENCE TO RELATED APPLICATIONS

This application is a Continuation of PCT International Application No. PCT/JP2018/040541 filed on Oct. 31, 2018, which claims priority under 35 U.S.C § 119(a) to Japanese Patent Application No. 2017-212172 filed on Nov. 1, 2017. Each of the above applications is hereby expressly incorporated by reference, in its entirety, into the present application.

BACKGROUND OF THE INVENTION

1. Field of the Invention

The present invention relates to a biopsy support device, an endoscope device, a biopsy support method, and a biopsy support program.

2. Description of the Related Art

In medical sites, a living tissue, such as a polyp, is sampled from the inside of a living body, and pathological inspection, biochemical analysis, genomic analysis, and the like are performed on the living tissue.

In the inspection of a digestive organ or the like using an endoscope device, a plurality of living tissues may be sampled in a single inspection. In this case, as described in JP2001-095749A, JP2006-230490A, and WO2006/038634 below, the sampled living tissues are managed in association with captured images in a case where the living tissues are sampled. This is important for performing highly accurate diagnosis.

JP2001-095749A describes a system in which, in a case where it is recognized that a living tissue has been sampled on the basis of an operation signal of a sampling instrument for sampling the living tissue, the number of the living tissue, a captured image at the time of sampling, and the like are recorded as the data of the sampled living tissue.

JP2006-230490A describes a system in which, in a case where the sampling instrument passes through a place where a wireless tag writer is installed after a living tissue has been sampled by the sampling instrument for sampling the living tissue, a captured image when the living tissue is sampled, a time point at which the living tissue has been sampled, and identification information associated with patient information or the like are written on the wireless tag fixed to the sampling instrument.

WO2006/038634 describes a system in which, in a case where a living tissue is sampled using a sampling instrument for sampling the living tissue and a sampling determination button is pressed, the living tissue is discharged into a container to which identification information is added, and the identification information of the container is associated with a captured image at the time of sampling the living tissue.

SUMMARY OF THE INVENTION

As described in JP2001-095749A, in the method of recognizing that the living tissue has been sampled on the basis of the operation signal of the sampling instrument, in a case where an operating member for operating the sampling instrument is erroneously operated, there is a possibility that erroneous recognition will occur. Additionally, in this method, a configuration for transmitting the operation signal of the sampling instrument to the control unit is required, and cost is required for system construction.

As described in JP2006-230490A, in the method of recognizing that the living tissue has been sampled by inserting and removing the sampling instrument, for example, in a case where the use of the sampling instrument is stopped halfway, there is a possibility that erroneous recognition will occur.

As described in WO2006/038634, in the method of recognizing that the living tissue has been sampled by pressing the sampling determination button, in a case where the sampling determination button is erroneously operated, there is a possibility that erroneous recognition will occur. Additionally, in this method, there are, for example, problems that the operation of the sampling determination button is cumbersome, and extra cost for the sampling determination button is involved.

The invention has been made in view of the above circumstances, and an object thereof is to provide a biopsy support device, an endoscope device comprising the same, a biopsy support method, and a biopsy support program capable of accurately recognizing that a living tissue has been sampled and improving diagnostic accuracy by inspection using the living tissue.

The biopsy support device of the invention is a biopsy support device that supports an inspection using a living tissue sampled by a sampling instrument for sampling a living tissue, which is used by being inserted into an endoscope having an imaging element, the biopsy support device comprising a sampling recognition unit that recognizes that the living tissue has been sampled by the sampling instrument on the basis of captured image data obtained by capturing an image using the imaging element; and an identification information generation unit that generates identification information corresponding to a living tissue in a case where the sampling recognition unit recognizes that the living tissue has been sampled.

An endoscope device according to the invention comprises the biopsy support device and the endoscope.

The biopsy support method of the invention is a biopsy support method of supporting an inspection using a living tissue sampled by a sampling instrument for sampling a living tissue, which is used by being inserted into an endoscope having an imaging element, the biopsy support method comprising a sampling recognition step of recognizing that the living tissue has been sampled by the sampling instrument on the basis of captured image data obtained by capturing an image using the imaging element; and an identification information generation step of generating identification information corresponding to a living tissue in a case where it is recognized that the living tissue has been sampled in the sampling recognition step.

The biopsy support program of the invention is a biopsy support program of supporting an inspection using a living tissue sampled by a sampling instrument for sampling a living tissue, which is used by being inserted into an endoscope having an imaging element, the biopsy support program causes a computer to execute: a sampling recognition step of recognizing that the living tissue has been sampled by the sampling instrument on the basis of captured image data obtained by capturing an image using the imaging element; and an identification information generation method of generating identification information corresponding to a living tissue in a case where it is recognized that the living tissue has been sampled in the sampling recognition step.

According to the invention, it is possible to provide the biopsy support device, the endoscope device comprising the biopsy support device, and the biopsy support method and the biopsy support program capable of accurately recognizing that a living tissue has been sampled and improving diagnostic accuracy by an inspection using the living tissue.

DESCRIPTION OF THE PREFERRED EMBODIMENTS

Hereinafter, embodiments of the invention will be described with reference to the drawings.

Figure 1:
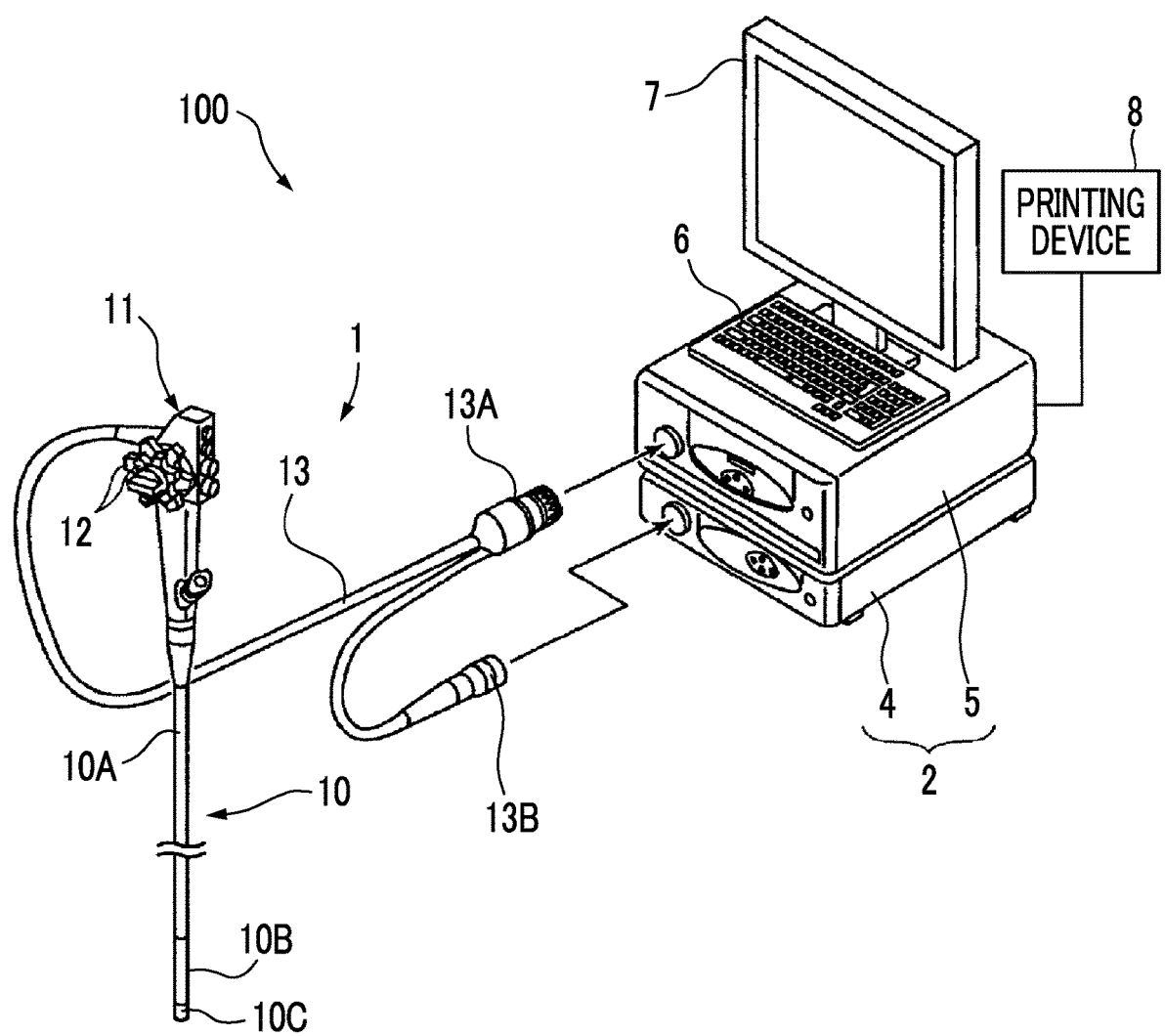
FIG. 1 is a view illustrating a schematic configuration of an endoscope device 100 that is an embodiment of the invention.

FIG. 1 is a view illustrating a schematic configuration of an endoscope device 100 that is an embodiment of the invention.

As illustrated in FIG. 1, the endoscope device 100 comprises an endoscope 1, and a body part 2 including a control device 4 and a light source device 5 to which the endoscope 1 is connected.

A display device 7 that displays a captured image or the like, an input unit 6 that is an interface for inputting various kinds of information to the control device 4, and a printing device 8 that performs printing on a seal attached to a storage container to be described below are connected to the control device 4. The control device 4 controls the endoscope 1, the light source device 5, the display device 7, and the printing device 8.

The endoscope 1 comprises an insertion part 10 that is a tubular member extending in one direction and is inserted into a subject, an operating part 11 that is provided at a proximal end part of the insertion part 10, an angle knob 12 provided adjacent to the operating part 11, and a universal cord 13 including connector parts 13A and 13B that attachably and detachably connect the endoscope 1 to the light source device 5 and the control device 4, respectively. The insertion part 10 is provided with operating members for performing an observation mode switching operation, an imaging and recording operation a forceps operation, an air and water supply operation, a suction operation, and the like.

In addition, although omitted in FIG. 1, various channels, such as a forceps hole 29 (refer to FIG. 3) for inserting biopsy forceps 28 that is a sampling instrument for sampling a living tissue, such as cells or polyps, an air and water supply channel, and a suction channel, are provided inside the operating part 11 and the insertion part 10.

The insertion part 10 is constituted of a flexible part 10A that has flexibility, a bending part 10B provided at a distal end of the flexible part 10A, and a hard distal end part 10C provided at a distal end of the bending part 10B.

The bending part 10B is configured to be bendable by the rotational movement operation of the angle knob 12. Depending on regions of the subject in which the endoscope 1 is used, the bending part 10B can be bent in an optional direction and at an optional angle and the distal end part 10C can be directed in a desired direction.

Figure 2:
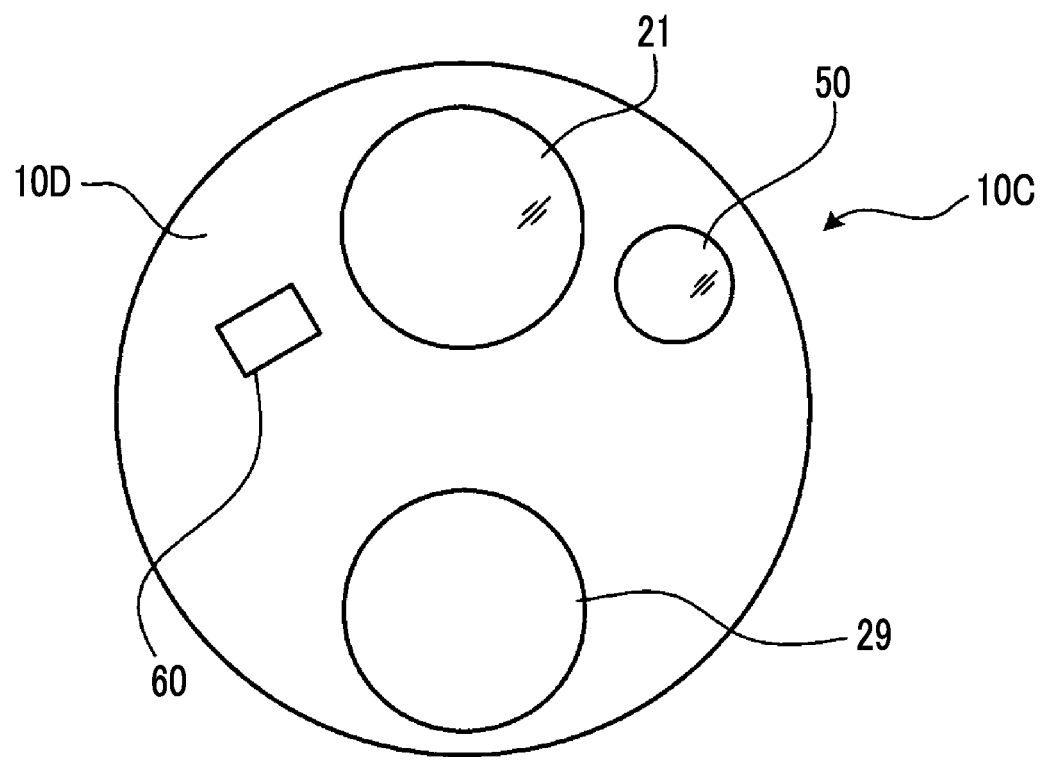
FIG. 2 is a front view of a distal end part 10C in the endoscope device 100 illustrated in FIG. 1.

FIG. 2 is a front view of the distal end part 10C in the endoscope device 100 illustrated in FIG. 1.

The distal end surface 10D of the distal end part 10C is substantially circular, and the distal end surface 10D is provided with an objective lens 21, an illumination lens 50, a forceps hole 29 for taking in and out the above-described biopsy forceps 28, and an air and water supply nozzle 60 for performing air and water supply.

Figure 3:
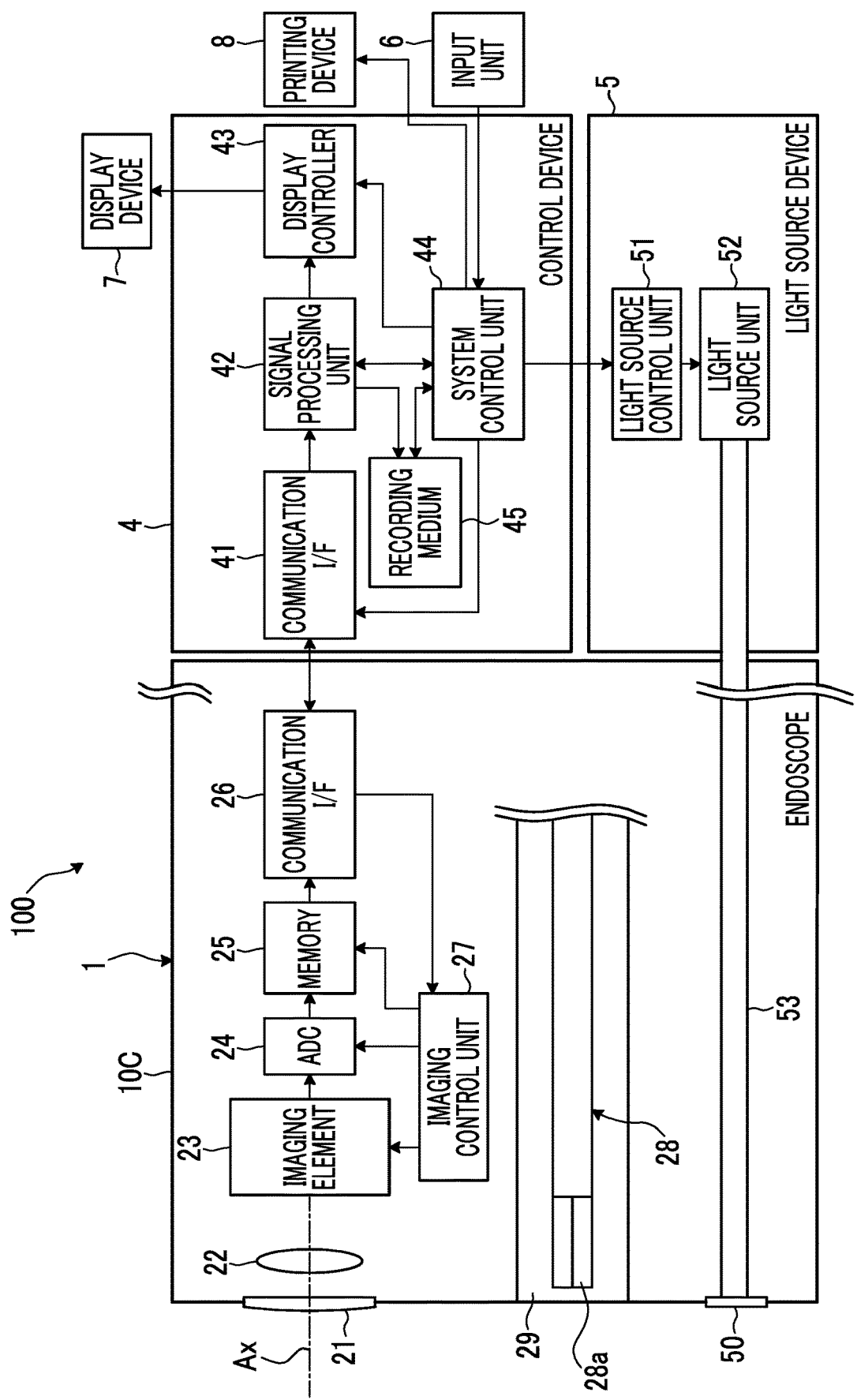
FIG. 3 is a schematic view illustrating an internal configuration of the endoscope device 100 illustrated in FIG. 1.

FIG. 3 is a schematic view illustrating an internal configuration of the endoscope device 100 illustrated in FIG. 1.

The light source device 5 comprises a light source control unit 51 and a light source unit 52.

The light source unit 52 generates illumination light for irradiating the subject. The illumination light emitted from the light source unit 52 enters a light guide 53 built in the universal cord 13, and is emitted to the subject through the illumination lens 50 provided at the distal end part 10C of the insertion part 10.

A white light source that emits white light, a plurality of light sources including the white light source and a light source (for example, a blue light source that emits blue light) that emits other color light, or the like is used as the light source unit 52. A plurality of illumination lenses 50 may be provided in conformity with the type of light emitted from the light source unit 52 on the distal end surface 10D of the distal end part 10C.

The light source control unit 51 is connected to a system control unit 44 of the control device 4. The light source control unit 51 controls the light source unit 52 on the basis of a command from the system control unit 44.

The distal end part 10C of the endoscope 1 is provided with the imaging optical system including the objective lens 21 and a lens group 22, an imaging element 23 that images the subject through the imaging optical system, an analog/digital converter circuit (ADC) 24, a memory 25, such as a random access memory (RAM), a communication interface (I/F) 26, an imaging control unit 27, the forceps hole 29 in which the biopsy forceps 28 is housed, and the light guide 53 for guiding the illumination light emitted from the light source unit 52 to the illumination lens 50.

The biopsy forceps 28 has an openable and closable gripping part 28a for gripping an object. The biopsy forceps 28 can grip a living tissue by two movable parts constituting the gripping part 28a.

The light guide 53 extends from the distal end part 10C to the connector part 13A of the universal cord 13. The illumination light emitted from the light source unit 52 of the light source device 5 is allowed to enter the light guide 53 in a state where the connector part 13A of the universal cord 13 is connected to the light source device 5.

As the imaging element 23, a charge coupled device (CCD) image sensor or a complementary metal oxide semiconductor (CMOS) image sensor is used.

The imaging element 23 has a light-receiving surface on which a plurality of pixels are two-dimensionally arranged, converts an optical image formed on the light-receiving surface by the above imaging optical system into an electrical signal (imaging signal) in each pixel, and outputs the converted electrical signal to the ADC 24. As the imaging element 23, for example, one on which color filters, such as an elementary color or a complementary color, are mounted, is used. A set of the imaging signals output from the respective pixels of the light-receiving surface of the imaging element 23 is referred to as captured image signals.

In addition, in a case where one in which the spectrum of the white light emitted from the white light source is divided in a time-division manner by a plurality of color filters to generate the illumination light is used as the light source unit 52, one on which no color filter is mounted may be used as the imaging element 23.

The imaging element 23 may be disposed at the distal end part 10C in a state where the light-receiving surface is perpendicular to an optical axis Ax of the objective lens 21, or may be disposed at the distal end part 10C in a state where the light-receiving surface is parallel to the optical axis Ax of the objective lens 21.

The imaging optical system provided in the endoscope 1 is constituted of optical members (including the above lens group 22), such as a lens and a prism, which are present on an optical path of the light from the subject between the imaging element 23 and the objective lens 21, and the objective lens 21. There is also a case where the imaging optical system is constituted of only the objective lens 21.

The ADC 24 converts the imaging signal output from the imaging element 23 into a digital signal having a predetermined number of bits.

The memory 25 temporarily records the imaging signal digitally converted by the ADC 24.

The communication I/F 26 is connected to a communication interface (I/F) 41 of the control device 4. The communication I/F 26 transmits the imaging signal recorded in the memory 25 to the control device 4 through a signal line within the universal cord 13.

The imaging control unit 27 is connected to the system control unit 44 of the control device 4 via the communication I/F 26. The imaging control unit 27 controls the imaging element 23, the ADC 24, and the memory 25 on the basis of a command from the system control unit 44 to be received by the communication I/F 26.

The control device 4 comprises the communication I/F 41 connected to the communication I/F 26 of the endoscope 1 by the universal cord 13, a signal processing unit 42, a display controller 43, the system control unit 44, and a recording medium 45.

The communication I/F 41 receives the imaging signal transmitted from the communication I/F 26 of the endoscope 1 and transmits the imaging signal to the signal processing unit 42.

The signal processing unit 42 has a memory for temporarily recording an imaging signal received from the communication I/F 41 built therein, and processes captured image signals that are a set of the imaging signals recorded in the memory such as demosaicing processing or gamma-correction processing to generate captured image data in such a format that object recognition to be described below is allowed. The captured image data generated by the signal processing unit 42 is recorded on the recording medium 45, such as a hard disk or a flash memory.

The display controller 43 causes the display device 7 to display a captured image based on the captured image data generated by the signal processing unit 42.

The system control unit 44 controls the respective units of the control device 4, and sends commands to the imaging control unit 27 of the endoscope 1 and the light source control unit 51 of the light source device 5, and integrally controls the entire endoscope device 100.

The system control unit 44 performs the control of the imaging element 23 via the imaging control unit 27. Additionally, the system control unit 44 performs the control of the light source unit 52 via the light source control unit 51.

The system control unit 44 includes various processors that execute a program to perform processing, a random access memory (RAM), and a read only memory (ROM).

The various processors include a central processing unit (CPU) that is a general-purpose processor that executes a program to perform various kinds of processing, a programmable logic device (PLD), which is a processor capable of changing a circuit configuration after manufacture, such as a field programmable gate array (FPGA), or an exclusive electric circuit, which is a processor having a circuit configuration exclusively designed to execute specific processing, such as an application specific integrated circuit (ASIC).

The structure of these various processors is, more specifically, an electric circuit in which circuit elements, such as semiconductor elements, are combined together.

The system control unit 44 may be constituted of one of the various processors, or may be constituted of a combination (for example, a combination of a plurality of FPGAs or a combination of a CPU and an FPGA) of two or more processors of the same type or different types.

Figure 4:
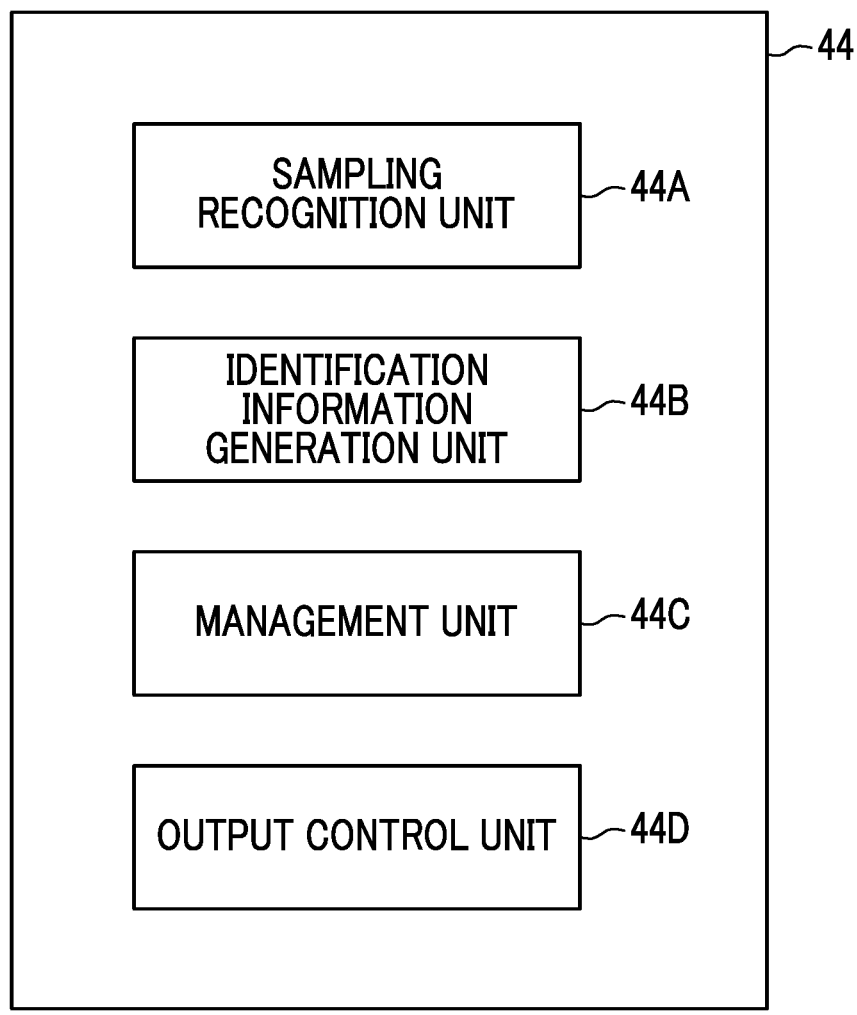
FIG. 4 is a view illustrating functional blocks of a system control unit 44 of the control device 4 illustrated in FIG. 3.

FIG. 4 is a view illustrating functional blocks of the system control unit 44 of the control device 4 illustrated in FIG. 3.

The processor of the system control unit 44 executes a biopsy support program stored in the ROM built in the system control unit 44, thereby functioning as a biopsy support device comprising a sampling recognition unit 44A, an identification information generation unit 44B, a management unit 44C, and an output control unit 44D.

The sampling recognition unit 44A performs the object recognition processing of recognizing whether or not a specific object is included from the captured image data on the basis of the captured image data obtained by processing the imaging signals, which are obtained by imaging the inside of a living body by the imaging element 23, by the signal processing unit 42. Based on the result of the object recognition processing, it is recognized that the living tissue has been sampled by the biopsy forceps 28.

Figure 5:
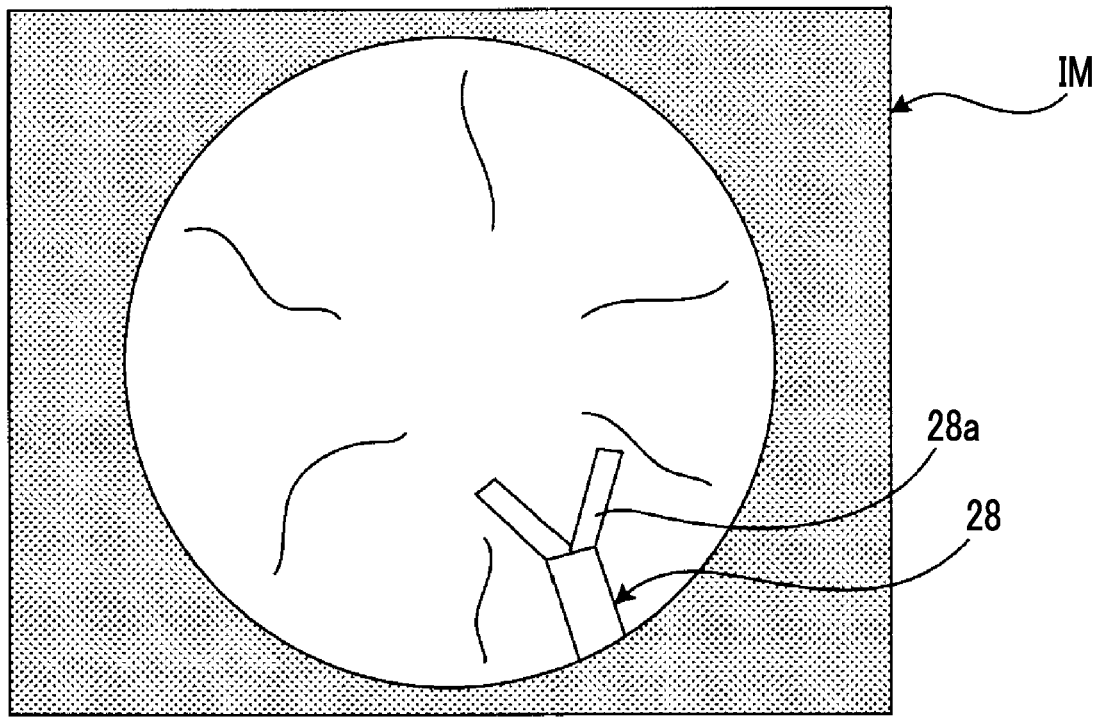
FIG. 5 is a view illustrating an example of captured image data IM obtained by imaging the inside of a living body with an imaging element 23 in a state where biopsy forceps 28 protrude from a forceps hole 29.

FIG. 5 is a view illustrating an example of captured image data IM obtained by imaging the inside of the living body with the imaging element 23 in a state where the biopsy forceps 28 protrudes from the forceps hole 29. In the example illustrated in FIG. 5, the captured image data IM includes image information of the biopsy forceps 28 in a state where the gripping part 28a is open.

The sampling recognition unit 44A extracts a feature amount from the captured image data IM exemplified in FIG. 5, and determines whether or not the biopsy forceps 28 is included in the captured image data IM, using the feature amount. Then, in a case where the biopsy forceps 28 are determined to been included in the captured image data IM, the sampling recognition unit 44A recognizes that the living tissue has been sampled by the biopsy forceps 28.

Figure 6:
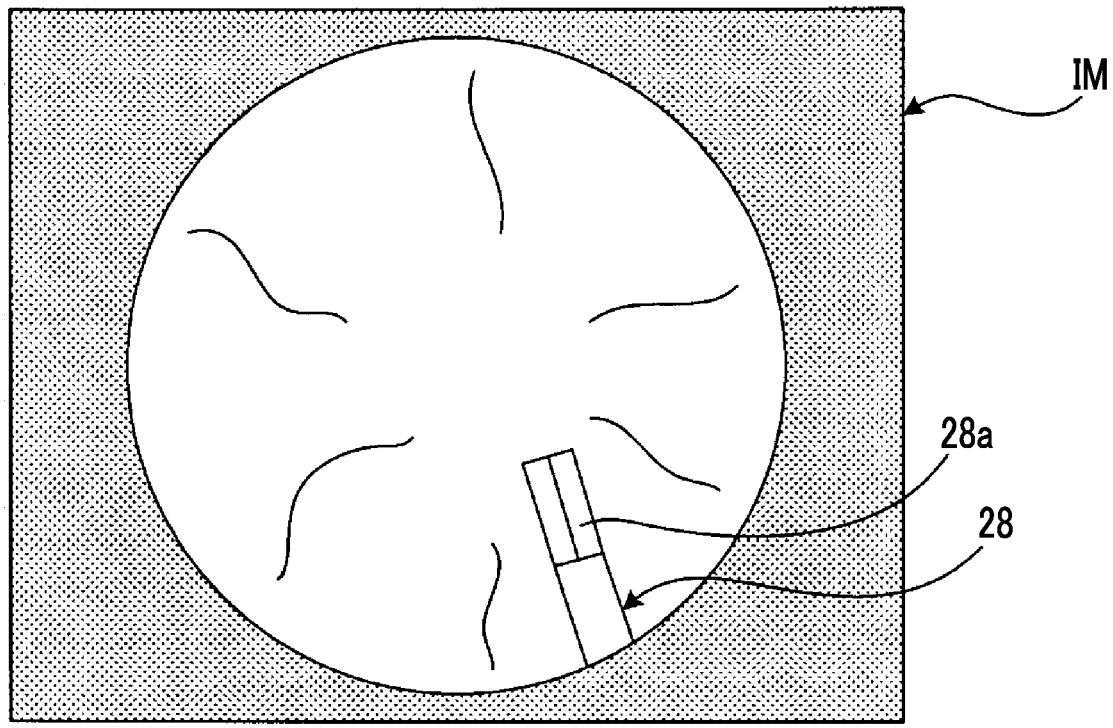
FIG. 6 is a view illustrating an example of the captured image data IM obtained by imaging the living body with the imaging element 23 in a state where the biopsy forceps 28 protrude from the forceps hole 29.

In addition, as illustrated in FIG. 6, in a case where the biopsy forceps 28 in a state where the gripping part 28a is closed are determined to be included in the captured image data IM, the sampling recognition unit 44A may recognize that the living tissue has been sampled by the biopsy forceps 28. Since the biopsy forceps 28 grips the living tissue by closing the gripping part 28a, according to this method, the fact that the living tissue has been sampled by the biopsy forceps 28 can be recognized with higher precision.

Figure 7:
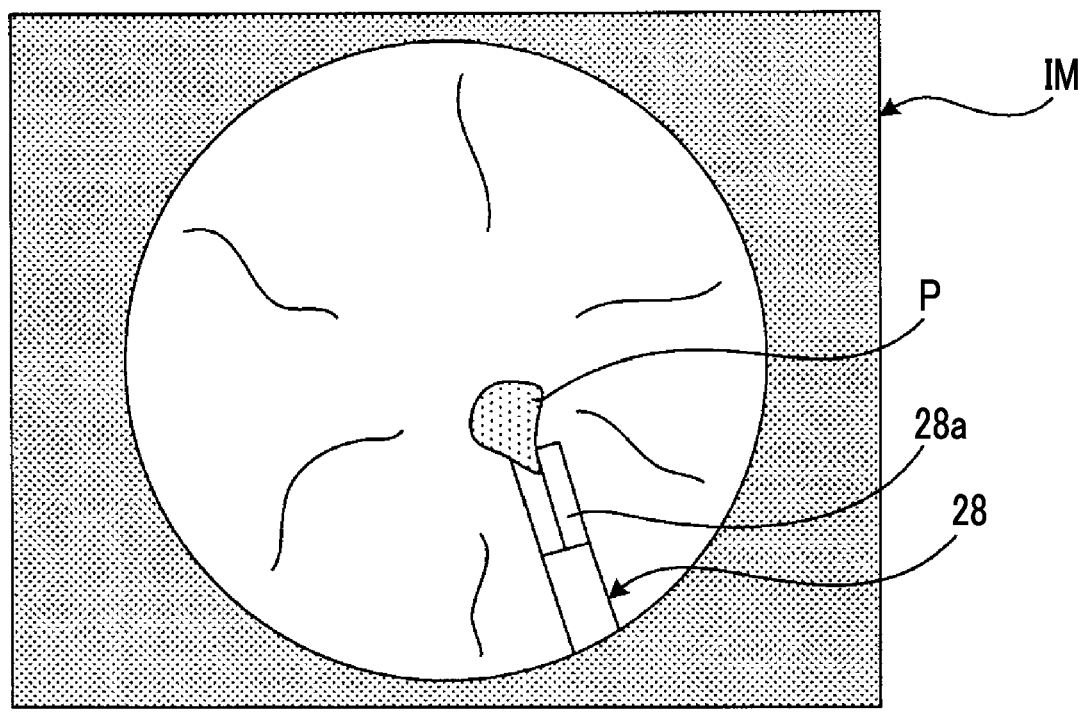
FIG. 7 is a view illustrating an example of the captured image data IM obtained by imaging the living body with the imaging element 23 in a state where the biopsy forceps 28 protrude from the forceps hole 29.

Additionally, as illustrated in FIG. 7, in a case where the biopsy forceps 28 in a state where an object P is gripped by the gripping part 28a is determined to be included in the captured image data IM, the sampling recognition unit 44A may recognize that the living tissue has been sampled by the biopsy forceps 28. Since the biopsy forceps 28 grips the living tissue by closing the gripping part 28a, according to this method, the fact that the living tissue has been sampled by the biopsy forceps 28 can be recognized with even higher precision.

Examples of the feature amount include brightness distribution, wavelets, pixel differences, histograms of oriented gradients (HOG), speeded up robust features (Joint HOG, SURF), edge of orientation histograms (EOH), scaled invariance feature transform (SIFT), Haar-like, which is a scalar quantity obtained as a difference value of average brightness of a rectangular region, Joint Haar-like, sparse features, co-occurrence probability features, or Shapelet features focused on edge relevance in a plurality of local regions.

The sampling recognition unit 44A determines whether or not the captured image data includes an object to be recognized through, for example, a technique, such as template matching, principal component analysis (PCA), neural network, linear discrimination distribution, support vector machine, boosting, adaptive boosting (Adaboost), or Real Adaboost, using these feature amounts. The sampling recognition unit 44A may perform object recognition by deep learning.

The identification information generation unit 44B illustrated in FIG. 4 generates identification information corresponding to a living tissue in a case where the sampling recognition unit 44A recognizes that the living tissue has been sampled.

The identification information may be any information from which an object can be identified, and an information group including a plurality of pieces of information lined up in accordance with predetermined order, such as Japanese alphabets (A, I, U, E, O, . . . ), English alphabets (A, B, C, D, E, . . . ), hiragana character strings (i, ro, ha, ni, ho, . . . ) that are lined up in accordance with the Iroha order of Japanese, or numerical strings (0, 1, 2, 3, 4, . . . ) including numbers that increase by a predetermined number (for example, "1"), is preferably used.

The identification information generation unit 44B sets any of a plurality of pieces of information constituting this information group as the initial information. With this initial information as a starting point, the identification information generation unit 44B sequentially changes the information within the information group to the next information and generates the changed information as the identification information every time the living tissue is recognized to have been sampled by the sampling recognition unit 44A. As the initial information, predetermined information is used.

For example, if the information group is the above-described numerical strings and the initial information is "0", "1" lined up next to "0" is generated as the identification information in a case where it is recognized that the living tissue has been sampled by the sampling recognition unit 44A. Then, in a case where it is recognized that the next living tissue has been sampled, "2" lined up next to "1" is generated as the identification information. In this way, whenever it is recognized that the living tissue has been sampled, the identification information is sequentially updated in accordance with the sequence of the numerical strings.

Alternatively, for example, if the information group is the above alphabet and the initial information is "A", "B" lined up next to "A" is generated as the identification information in a case where it is recognized that the living tissue has been sampled by the sampling recognition unit 44A. Then, in a case where it is recognized that the next living tissue has been sampled, "C" lined up next to "B" is generated as the identification information. In this way, whenever it is recognized that the living tissue has been sampled, the identification information is sequentially updated in accordance with the sequence of the alphabets.

In addition, the identification information may be a combination of the information determined by the updating as described above and personal information (name, patient number, and the like) of the subject.

The management unit 44C illustrated in FIG. 4 records the identification information generated by the identification information generation unit 44B in association with the captured image data generated by the signal processing unit 42 and recorded on the recording medium 45. The captured image data associated with the identification information is an image data captured in a period including a time point at which it is recognized that a living tissue corresponding to the identification information has been sampled.

The period including the time point at which it is recognized that the living tissue has been sampled may be a period in which it is possible to check where and in what state the sampled living tissue is present within the living body.

For example, in a case where a time point at which the sampling recognition unit 44A recognizes that the living tissue has been sampled is defined as a time point t0, this period can be a period between the time point t0 and a first time point t1 before a first time from the time point t0. This period can also be a period between a second time point t2 before a second time from the time point t0 and a third time point t3 after a third time from the point time point t0.

The management unit 44C may set the first time or the second time and the third time to the time which the operator of the endoscope 1 inputs to the input unit 6, or may set the first time or the second time and the third time to a fixed value predetermined on the system side.

The captured image data obtained in the above period may be all captured image data (moving image data)

obtained during this period, or may be still image data obtained by extracting a portion of all the captured image data. Additionally, the management unit 44C may record the identification information in association with the captured image data obtained at the time point t0.

In a case where the identification information is generated by the identification information generation unit 44B, the output control unit 44D causes the identification information to be output from the printing device 8 serving as an output device.

Specifically, in a case where the identification information is generated by the identification information generation unit 44B, the output control unit 44D outputs the identification information to the printing device 8, and causes the printing device 8 to directly output the identification information or output a seal printed by coding the identification information.

This seal is attached to a storage container for storing the living tissue by staff involved in the inspection. Then, the living tissue corresponding to the identification information printed on the seal (the living tissue sampled at the time point at which the seal is output) is stored in the storage container. By the control of the output control unit 44D and the work of the staff members, the storage container storing the living tissue corresponding to the identification information is associated with the identification information.

In addition, the printing device 8 may print the identification information on the storage container itself instead of the seal. Additionally, instead of the above-described seal, a wireless tag on which the identification information is written may be used. In this case, a writing device that writes information to the wireless tag is used as the output device instead of the printing device 8.

Additionally, the attachment of the seal or the wireless tag to the storage container may be performed automatically instead of manually by a machine connected to the control device 4.

Alternatively, there is a place where a number of empty storage containers are arranged, and the system control unit 44 may recognize that an object has been put into any of these storage containers by using a sensor or a camera, and automatically attaches the above-mentioned seal or wireless tag to the storage container into which the object has been put, thereby performing the association between the identification information and the storage container.

Next, the operation of the endoscope device 100 configured as described above will be described.

Figure 8:
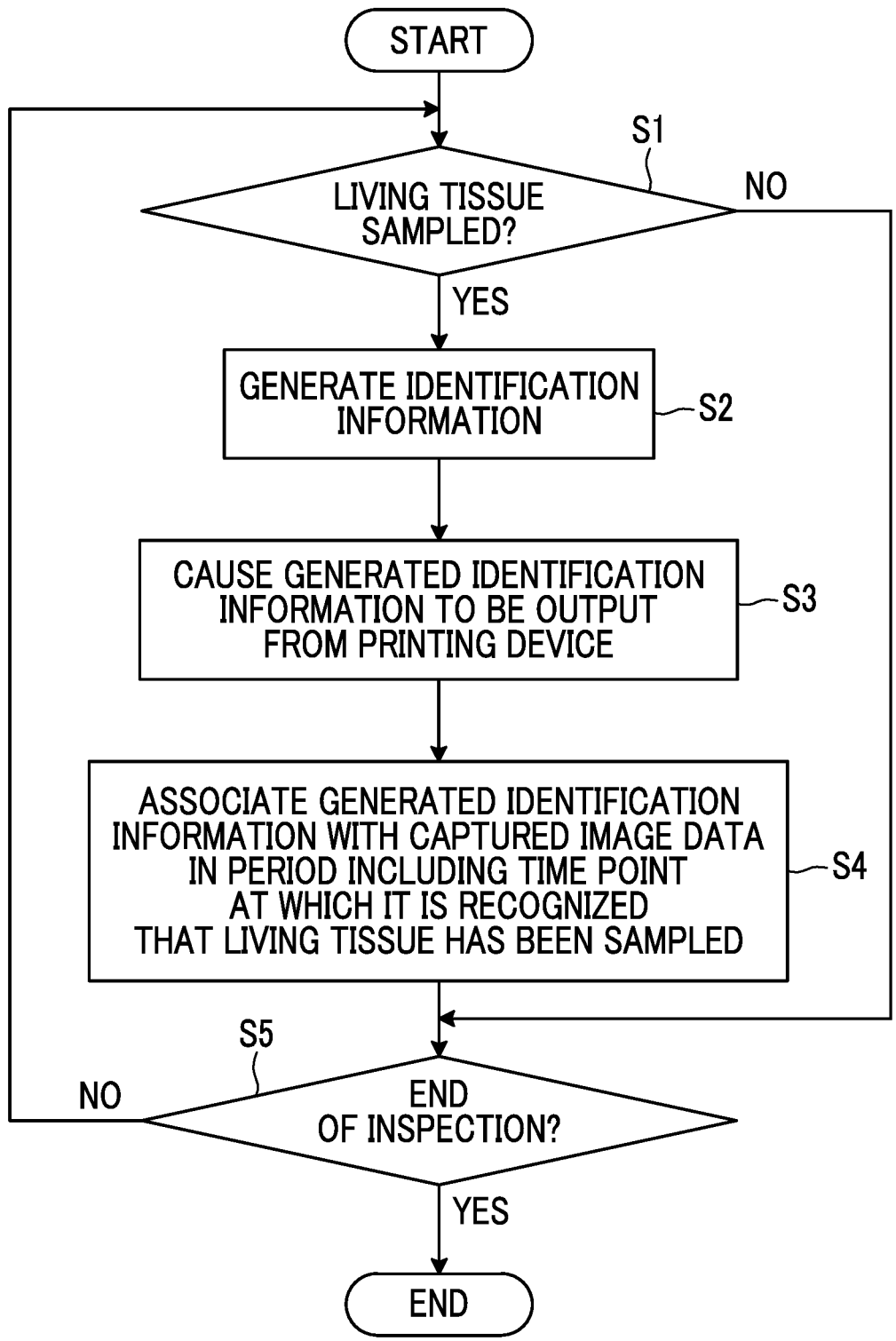
FIG. 8 is a flowchart for explaining the operation of a system control unit 44 illustrated in FIG. 4.

FIG. 8 is a flowchart for explaining the operation of the system control unit 44 illustrated in FIG. 4.

In a case where the capturing of the moving image by the imaging element 23 is started by the operation of the operating part 11, the captured image signals are output from the imaging element 23, the captured image signals are processed, and the captured image data for one frame of the moving image is sequentially generated and recorded on the recording medium 45. Additionally, a live view image is displayed on the display device 7 on the basis of the captured image data sequentially generated in this way.

In a case where the imaging of the moving image is started, the sampling recognition unit 44A sequentially acquires the captured image data generated by the signal processing unit 42, and analyzes the acquired data to determine whether or not the living tissue has been sampled by the biopsy forceps 28 (Step S1).

In a case where it is determined that the living tissue has not been sampled by the biopsy forceps 28 (Step S1: NO), the processing proceeds to Step S5 to be described below.

On the other hand, in a case where the sampling recognition unit 44A determines that the living tissue has been sampled by the biopsy forceps 28 and recognizes that the living tissue has been sampled (Step S1: YES), the identification information generation unit 44B generates the identification information corresponding to the living tissue on which the sampling has been recognized (Step S2). In Step S2, for example, in a case where the initial information is "0", "1" is generated as the identification information.

In a case where the identification information is generated in Step S2, the output control unit 44D outputs the generated identification information to the printing device 8, and a seal on which the identification information generated in Step S2 is printed is generated by the printing device 8 (Step S3).

Additionally, in a case where the identification information is generated in Step S2, the management unit 44C records the generated identification information in association with the captured image data generated in the period including the time point at which the determination of Step S1 is YES and it is recognized that the living tissue has been sampled, in the captured image data recorded on the recording medium 45 (Step S4).

After Step S4, in a case where an instruction to end imaging by the imaging element 23 is performed and the inspection is ended (Step S5: YES), the system control unit 44 ends the processing. On the other hand, in a case where the inspection is continued (Step S5: NO), the processing returns to Step S1, and the subsequent processing is repeated.

By the above processing, for example, assuming that the operator who operates the endoscope 1 samples a total of three living tissue from the body of the subject with the biopsy forceps 28, a storage container storing a firstly sampled living tissue is in a state where a seal printed with identification information ("1") corresponding to the living tissue is attached, a storage container storing a secondly sampled living tissue is in a state where a seal printed with identification information ("2") corresponding to the living tissue is attached, and a storage container storing a last sampled living tissue is in a state where a seal printed with identification information ("3") corresponding to the living tissue is attached.

Additionally, in the captured image data recorded on the recording medium 45 by this inspection, the identification information ("1") is recorded in association with the captured image data in the period including the time point at which it is recognized that the living tissue corresponding to the identification information ("1") has been sampled, the identification information ("2") is recorded in association with the captured image data in the period including the time point at which it is recognized that the living tissue corresponding to the identification information ("2") has been sampled, and the identification information ("3") is recorded in association with the captured image data in the period including the time point at which it is recognized that the living tissue corresponding to the identification information ("3") has been sampled.

Then, for example, a pathological test result of a living tissue stored in a storage container on which a seal on which identification information is printed is attached is managed in association with the identification information.

Hence, while associating the pathological test result of the living tissue with the captured image data obtained in a predetermined period including the time point at which the living tissue has been sampled, it is possible to determine the disease of the subject, and an accurate diagnosis can be performed.

The endoscope device 100 recognizes that the living tissue has been sampled by the biopsy forceps 28 on the basis of the captured image data. For this reason, the operator of the endoscope 1 can associate a living tissue, captured image data obtained in a case where the living tissue is sampled, and identification information of the living tissue with each other without performing a special operation. For this reason, the burden on the operator at the time of inspection can be reduced. Additionally, since a dedicated mechanism for notifying the system control unit 44 that the living tissue has been sampled is not required, the cost of the endoscope device 100 or the size of the endoscope 1 can be reduced.

Additionally, according to the endoscope device 100, the presence or absence of sampling of a living tissue is determined on the basis of the captured image data. Therefore, for example, in a case where the biopsy forceps 28 is sent out from the forceps hole 29 but the living tissue is not sampled, in a case where an operation is performed in a state where the biopsy forceps 28 is not sent out from the forceps hole 29, or the like, it is possible to prevent the erroneous recognition that the living tissue has been sampled.

For example, in a method of determining whether or not the living tissue is sampled depending on whether or not the biopsy forceps 28 are included in the captured image data, in a case where the time during which the biopsy forceps 28 are included in the captured image data is equal to or greater than a threshold value, it is determined that the living tissue has been sampled. In this way, it is possible to identify whether or the biopsy forceps 28 have been sent out in an attempt to sample the living tissue, or whether or the biopsy forceps 28 has been sent out for a purpose other than the erroneous operation or sampling. For this reason, it is possible to accurately determine whether or not the living tissue has been sampled.

In the description up to this point, as the sampled living tissue is stored in a storage container, and a seal printed with identification information corresponding to the living tissue is attached to the storage container, the identification information corresponding to the living tissue is associated with the storage container.

Figure 9:
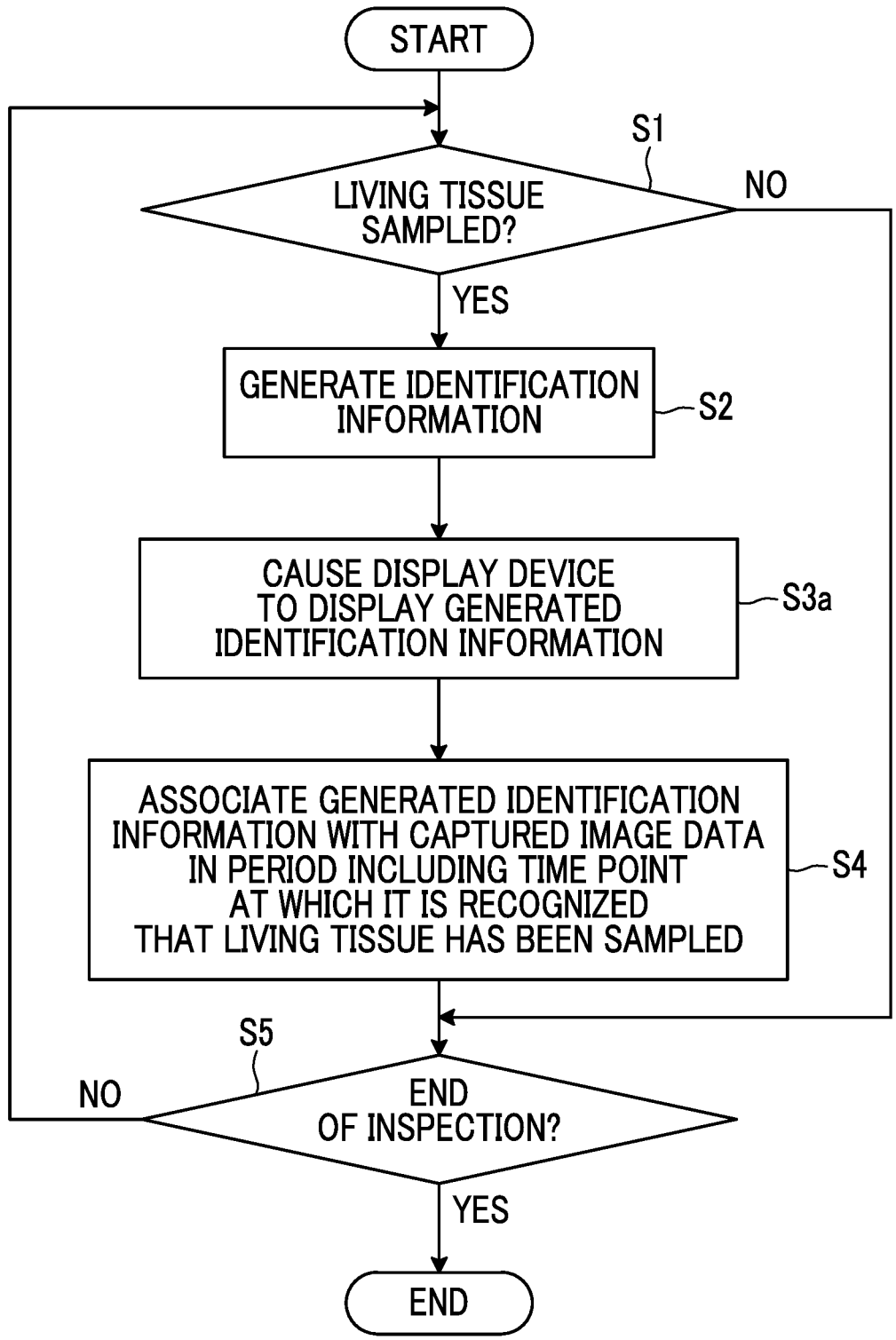
FIG. 9 is a flowchart for explaining a first modification example of the operation of the system control unit 44 illustrated in FIG. 4.

As a modification example, empty storage containers with seals, on which a plurality of pieces of identification information capable of being generated by the identification information generation unit 44B is printed, is prepared in advance. Then, the operator of the endoscope 1 stores a sampled living tissue to the storage container with the seal on which the identification information corresponding to the sampled living tissue is printed. By this way the identification information and the storage container prepared in advance may be associated with each other FIG. 9 is a flowchart for explaining a first modification example of the operation of the system control unit 44 illustrated in FIG. 4. In the first modification example, the printing device 8 is not connected to the control device 4. Additionally, at the time of inspection, it is assumed that a plurality of empty storage containers to which seals on which the identification information generated by the identification information generation unit 44B is printed are attached are prepared in advance. In FIG. 9, the same processing as that in FIG. 8 is denoted by the same reference numerals, and the description thereof will be omitted.

In a case where the identification information is generated in Step S2, the output control unit 44D of the system control unit 44 outputs the identification information generated in Step S2 to the display device 7 and causes the display device to display the output identification information (Step S3a).

The operator of the endoscope 1 stores the sampled living tissue in a storage container having a seal on which the identification information displayed in the process of Step S3a is printed. Accordingly, the identification information corresponding to the sampled living tissue is associated with the storage container.

After Step S3a, the processing after Step S4 is performed.

As described above, according to the first modification example, the work of attaching the seal during the inspection becomes unnecessary. Therefore, the burden at the time of the inspection can be reduced. Additionally, according to the first modification example, the identification information corresponding to the sampled living tissue can be checked on the display device 7 together with the live view image. For this reason, the living tissue can be prevented from being stored in another storage container, and the living tissue can be accurately managed.

In addition, in the first modification example, the storage container storing the living tissue and the identification information corresponding to the living tissue may be associated with each other by handwriting the identification information displayed on the display device 7 on the storage container in which the living tissue is stored instead of attaching a seal to the storage container. According to this configuration, a system for printing identification information on a seal is not required, and the cost for constructing a system for supporting biopsy can be reduced.

Additionally, in Step S3a of FIG. 9, the output control unit 44D included in the system control unit 44 may cause the display device 7 to display one piece of captured image data associated with the identification information in Step S4 as the still image instead of outputting the identification information generated in Step S2 to the display device 7. In this configuration, in Step S3a, the still image is displayed, for example, to be overlaid on the live view image displayed on the display device 7. By displaying the still image, the operator can know that the identification information has been associated with the captured image data.

Additionally, in Step S3a of FIG. 9, the output control unit 44D of the system control unit 44 may output the identification information generated in Step S2 to the display device 7, and may cause the display device 7 to display the one piece of captured image data as the still image. In this configuration, in Step S3a, the still image and the identification information are displayed to be, for example, overlaid on the live view image displayed on the display device 7. For this reason, by displaying the still image, the operator can know that the identification information has been associated with the captured image data. Additionally, the living tissue can be accurately managed by the displayed identification information.

Figure 10:
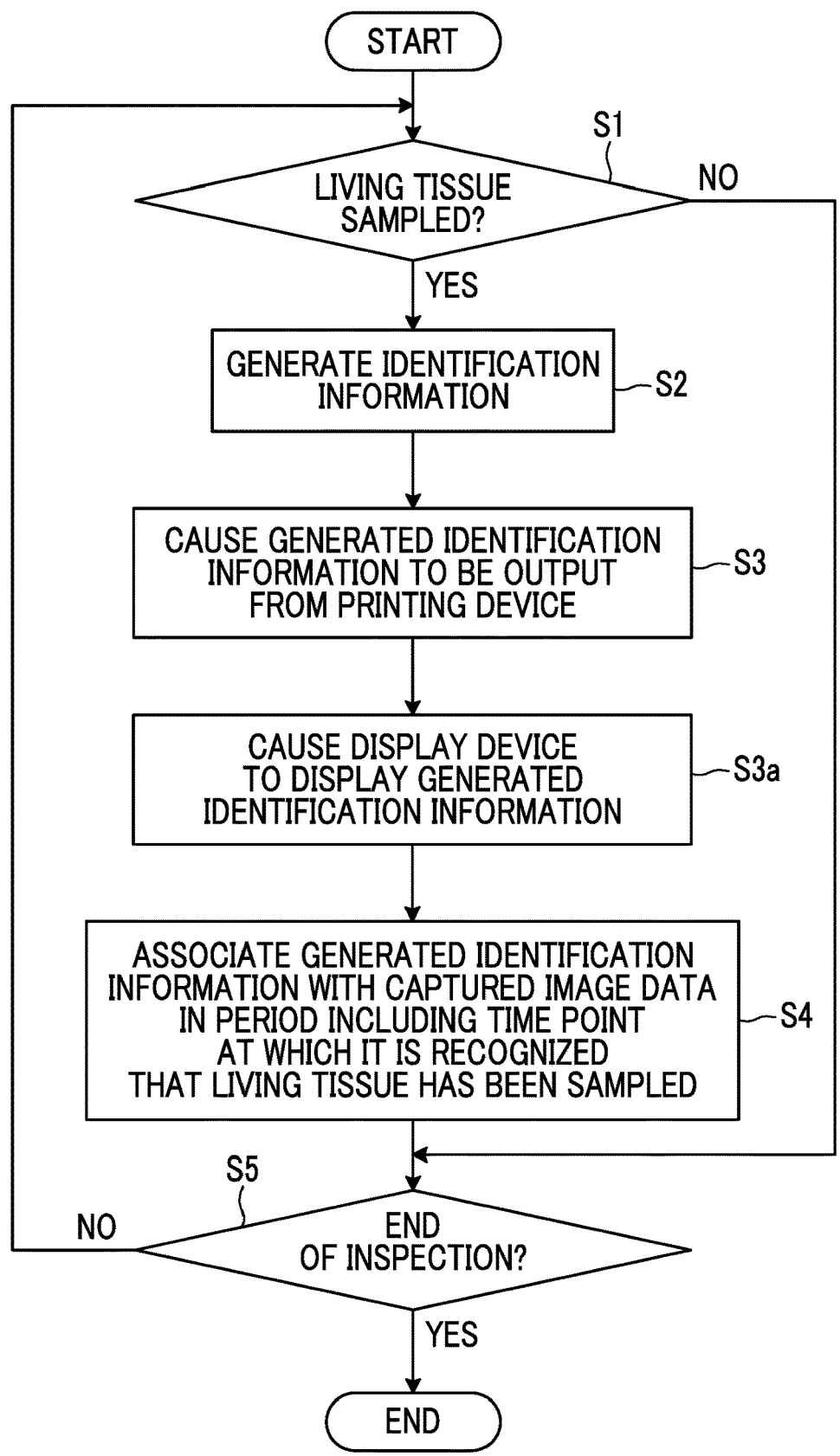
FIG. 10 is a flowchart for explaining a second modification example of the operation of the system control unit 44 illustrated in FIG. 4.

FIG. 10 is a flowchart for explaining a second modification example of the operation of the system control unit 44 illustrated in FIG. 4. The flowchart illustrated in FIG. 10 is the same as FIG. 8 except that Step S3a illustrated in FIG. 9 is added between Step S3 and Step S4. In FIG. 10, the same processing as that in FIG. 8 is denoted by the same reference numerals, and the description thereof will be omitted.

After Step S3, the output control unit 44D of the system control unit 44 outputs the identification information generated in Step S2 to the display device 7, and causes the output identification information to display the same (Step S3a). After Step S3a, the processing after Step S4 is performed.

In the second modification example, in a case where the operator of the endoscope 1 stores the sampled living tissue in an empty storage container, the staff attaches the seal output from the printing device 8 in Step S3 to this storage container. In this case, by comparing the identification information printed on the seal with the identification information displayed on the display device 7, the storage container storing the living tissue can be more accurately associated with the identification information corresponding to the living tissue.

In addition, even in Step S3a of FIG. 10, the output control unit 44D of the system control unit 44 may cause the display device 7 to display one piece of captured image data associated with the identification information in Step S4 as the still image instead of outputting the identification information generated in Step S2 to the display device 7.

Alternatively, in Step S3a of FIG. 10, the output control unit 44D of the system control unit 44 may output the identification information generated in Step S2 to the display device 7, and may cause the display device 7 to display the above one piece of captured image data as the still image.

As described above, according to the second modification example, the management of the living tissue can be more accurately performed.

Figure 11:
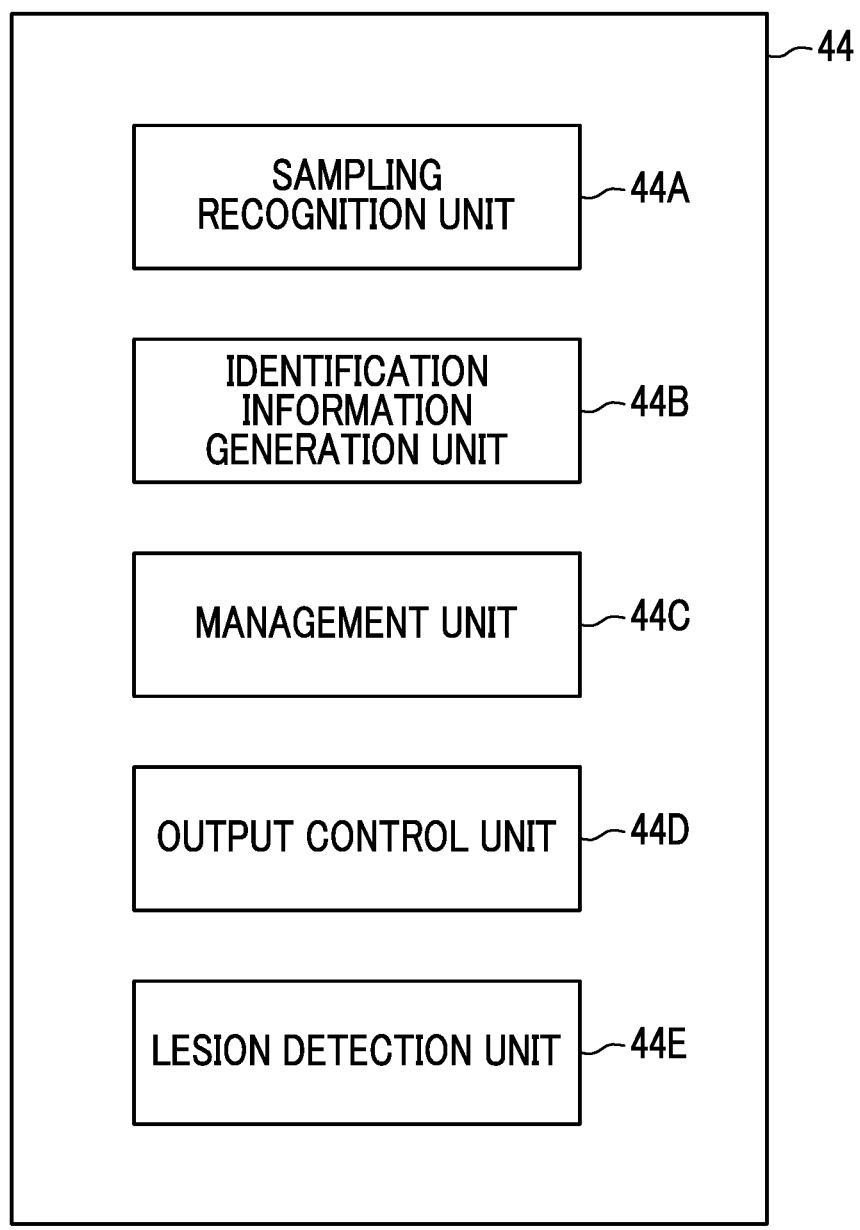
FIG. 11 is a view illustrating a modification example of the functional blocks of the system control unit 44 illustrated in FIG. 4.

FIG. 11 is a view illustrating a modification example of the functional blocks of the system control unit 44 illustrated in FIG. 4. In FIG. 11, the same components as those in FIG. 4 are denoted by the same reference numerals, and the description thereof will be omitted.

The processor of the system control unit 44 illustrated in FIG. 11 executes the biopsy support program stored in the ROM built in the system control unit 44, thereby functioning as the biopsy support device comprising the sampling recognition unit 44A, the identification information generation unit 44B, the management unit 44C, the output control unit 44D, and the lesion detection unit 44E.

The lesion detection unit 44E detects a lesion site, which is a site suspected of a lesion, by machine learning or the like from the captured image data recorded on the recording medium 45.

The management unit 44C of the system control unit 44 illustrated in FIG. 11 sets, as the above first time point, the time point at which the lesion site is first detected by the lesion detection unit 44E from the captured image data in which the sampling of the living tissue is recognized by the sampling recognition unit 44A.

Alternatively, the management unit 44C of the system control unit 44 illustrated in FIG. 11 may set, as the second time point, the time point at which the lesion site is first detected by the lesion detection unit 44E from the captured image data in which the sampling of the living tissue is recognized by the sampling recognition unit 44A, and may set, as the third time point, the time point at which this lesion site is not detected after the second time point.

Alternatively, the management unit 44C of the system control unit 44 illustrated in FIG. 11 may set, as the above second point, the time point at which the lesion site is first detected by the lesion detection unit 44E from the captured image data in which the sampling of the living tissue is recognized by the sampling recognition unit 44A. The management unit 44C may also set, as the third time point, the time point at which a sampling mark generated by sampling the living tissue at the lesion site with the biopsy forceps 28 is detected after this time point. This sampling mark may be detected from the captured image data recorded on the recording medium 45 by machine learning or the like.

In other words, the management unit 44C records the identification information generated by the identification information generation unit 44B at the time point at which the sampling of the living tissue is recognized by the sampling recognition unit 44A in association with some or all of all captured image data including the same lesion site as the lesion site detected by the lesion detection unit 44E (that is, the site including the sampled living tissue) at that time point.

According to the configuration of the system control unit 44 illustrated in FIG. 11, captured image data showing a site including a living tissue sampled by the biopsy forceps 28 can be extracted from the captured image data recorded on the recording medium 45. For this reason, highly accurate diagnosis can be performed by comprehensively considering the result of the pathological inspection of the living tissue and the captured image of the living tissue.

In addition, the configuration illustrated in FIG. 11 can be combined with the modification example illustrated in FIG. 9 or FIG. 10.

Figure 12:
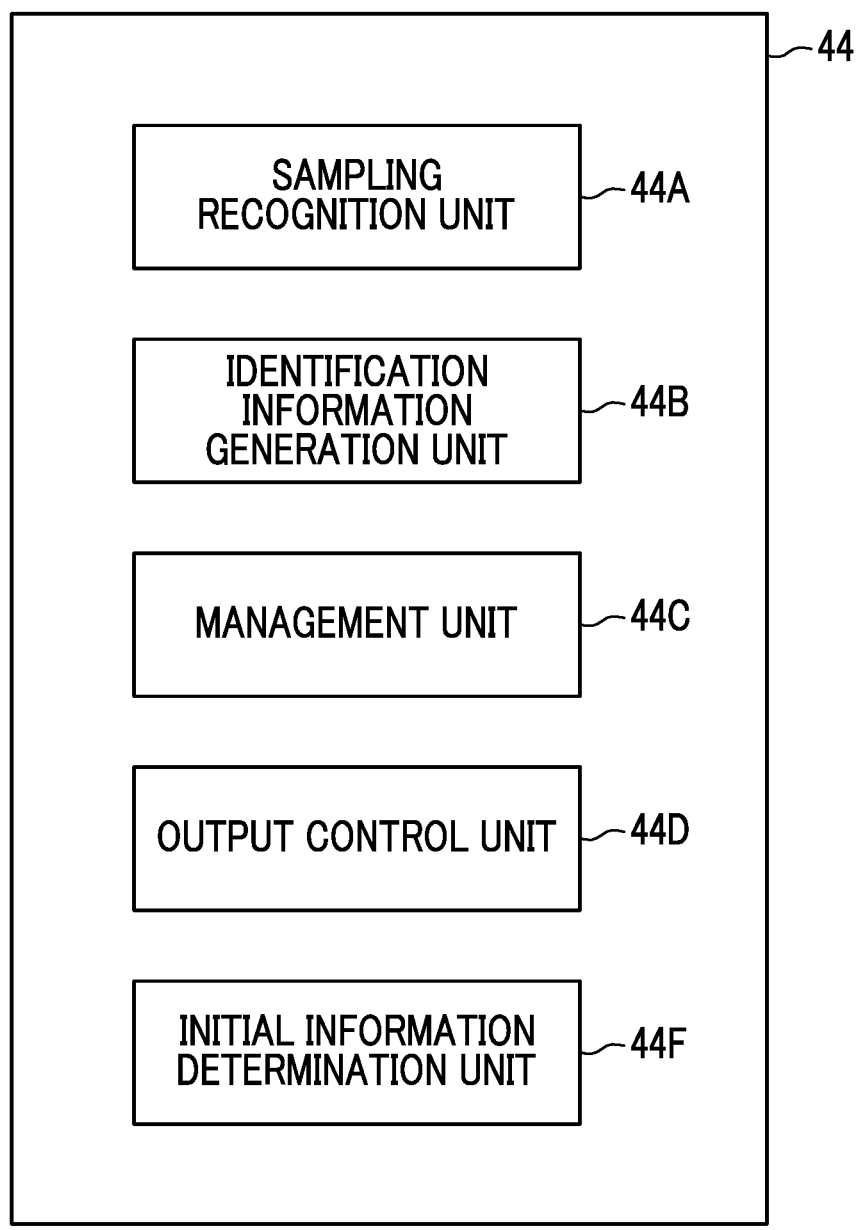
FIG. 12 is a view illustrating a modification example of the functional blocks of the system control unit 44 illustrated in FIG. 4.

FIG. 12 is a view illustrating a modification example of the functional blocks of the system control unit 44 illustrated in FIG. 4. In FIG. 12, the same components as those in FIG. 4 are denoted by the same reference numerals, and the description thereof will be omitted.

The processor of the system control unit 44 illustrated in FIG. 12 executes the biopsy support program stored in the ROM built in the system control unit 44, thereby functioning as the biopsy support device comprising the sampling recognition unit 44A, the identification information generation unit 44B, the management unit 44C, the output control unit 44D, and an initial information determination unit 44F.

The initial information determination unit 44F determines the initial information of the identification information set by the identification information generation unit 44B on the basis of the information input from the input unit 6.

For example, in a case where "1" or "A" is input as setting information of the initial information from the input unit 6, the initial information determination unit 44F determines the "1" or "A" as the initial information.

In this way, by enabling the initial information of the identification information to be optionally set manually, optimal management according to the inspection content can be performed. For example, in a case where two inspections are performed on the same subject, at the time of a second inspection, the last identification information generated in a first inspection is set as an initial value, so that the management of living tissues of the same subject becomes easy.

In addition, the configuration illustrated in FIG. 12 can be combined with the modification examples illustrated in FIGS. 9 to 11.

As described above, the following matters are disclosed in the present specification.

(1) A biopsy support device that supports an inspection using a living tissue sampled by a sampling instrument for sampling a living tissue, which is used by being inserted into an endoscope having an imaging element, the biopsy support device comprising: a sampling recognition unit that recognizes that the living tissue has been sampled by the sampling instrument on the basis of captured image data obtained by capturing an image using the imaging element; and an identification information generation unit that generates identification information corresponding to a living tissue in a case where the sampling recognition unit recognizes that the living tissue has been sampled.

(2) The biopsy support device according to (1), further comprising: a management unit that records the identification information generated by the identification information generation unit in association with the captured image data obtained in a period including a time point at which it is recognized that the living tissue corresponding to the identification information has been sampled.

(3) The biopsy support device according to (2), wherein the management unit sets, as the period, a period between the time point and a first time point before a first time from the time point.

(4) The biopsy support device according to (2), wherein the management unit sets, as the period, a period between a second time point before a second time from the time point and a third time point after a third time from the time point.

(5) The biopsy support device according to (3), further comprising: a lesion detection unit that detects a site suspected of a lesion from the captured image data, wherein the management unit sets a time point at which the site detected by the lesion detection unit at the time point is first detected by the lesion detection unit, as the first time point.

(6) The biopsy support device according to (4), further comprising: a lesion detection unit that detects a site suspected of a lesion from the captured image data, wherein the management unit sets a time point at which the site detected by the lesion detection unit at the time point is first detected by the lesion detection unit, as the second time point, and sets at a time point at which the site is not detected as the third time point.

(7) The biopsy support device according to (4), further comprising: a lesion detection unit that detects a site suspected of a lesion from the captured image data, wherein the management unit sets a time point at which the site detected by the lesion detection unit at the time point is first detected by the lesion detection unit, as the second time point, and sets a time point at which a sampling mark generated by sampling the living tissue at the site by the sampling instrument is detected, as the third time point.

(8) The biopsy support device according to any one of claims (1) to (7), further comprising: an output control unit that causes one or both of the identification information and the captured image data associated with the identification information to be output from an output device in a case where the identification information is generated by the identification information generation unit.

(9) The biopsy support device according to (8), wherein the output device is a display device on which a captured image based on the captured image data.

(10) The biopsy support device according to (8), wherein the output device includes a printing device that prints the identification information or a writing device that writes the identification information to a wireless tag, and wherein the output control unit outputs the identification information from the output device.

(11) The biopsy support device according to (8), wherein the output device is a display device on which a captured image based on the captured image data is displayed, and a printing device that prints the identification information or a writing device that writes the identification information to a wireless tag, and wherein the output control unit outputs the identification information from at least one of the display device or the writing device, and causes the captured image data associated with the identification information to be output from the display device.

(12) The biopsy support device according to any one of claims (1) to (11), wherein the sampling recognition unit recognizes that a living tissue has been sampled in a case where the sampling instrument is included in the captured image data.

(13) The biopsy support device according to any one of claims (1) to (11), wherein the sampling instrument has a gripping part for gripping an object, and wherein the sampling recognition unit recognizes that a living tissue has been sampled in a case where the sampling instrument in a state where the gripping part is closed is included in the captured image data.

(14) The biopsy support device according to any one of claims (1) to (11), wherein the sampling instrument has a gripping part for gripping an object, and wherein the sampling recognition unit recognizes that a living tissue has been sampled in a case where the sampling instrument in a state where the object is gripped by the gripping part is included in the captured image data.

(15) The biopsy support device according to any one of claims (1) to (14), wherein the identification information is any of the plurality of pieces of information lined up in a predetermined order, wherein the identification information generation unit sets any of a plurality of pieces of information as initial information, sequentially changes the information to next information with the initial information as a starting point whenever it is recognized that the living tissue has been sampled by the sampling recognition unit, and generates the changed information as the identification information, and wherein the biopsy support device further comprises a starting point information determining unit that determines the initial information on the basis of information input from an input unit for inputting information.

(16) The biopsy support device according to (15), wherein the identification information is a number or an alphabet.

(17) An endoscope device comprising: a biopsy support device according to any one of (1) to (16); and the endoscope.

(18) A biopsy support method of supporting an inspection using a living tissue sampled by a sampling instrument for sampling a living tissue, which is used by being inserted into an endoscope having an imaging element, the biopsy support method comprising: a sampling recognition step of recognizing that the living tissue has been sampled by the sampling instrument on the basis of captured image data obtained by capturing an image using the imaging element; and an identification information generation step of generating identification information corresponding to a living tissue in a case where it is recognized that the living tissue has been sampled in the sampling recognition step.

(19) A biopsy support program of supporting an inspection using a living tissue sampled by a sampling instrument for sampling a living tissue, which is used by being inserted into an endoscope having an imaging element, the biopsy support program causes a computer to execute: a sampling recognition step of recognizing that the living tissue has been sampled by the sampling instrument on the basis of captured image data obtained by capturing an image using the imaging element; and an identification information generation step of generating identification information corresponding to a living tissue in a case where it is recognized that the living tissue has been sampled in the sampling recognition step.

According to the invention, it is possible to provide the biopsy support device, the endoscope device comprising the biopsy support device, and the biopsy support method and the biopsy support program capable of accurately recognizing that a living tissue has been sampled and improving diagnostic accuracy by an inspection using the living tissue.

EXPLANATION OF REFERENCES

100: endoscope device
1: endoscope
2: body part
10: insertion part
10A: flexible part
10B: bending part
10C: distal end part
10D: distal end surface
11: operating Part
12: angle knob
13: universal cord
13A, 13B: connector part
6: input unit
7: display device
8: printing device
21: objective lens
Ax: optical axis
22: lens group
23: imaging element
24: ADC
25: memory
26: communication interface
27: imaging control unit
28: biopsy forceps
28a: gripping part
29: forceps hole
4: control device
41: communication interface
42: signal processing unit
43 display controller
44: system control unit
44A: sampling recognition unit
44B: identification information generation unit
44C: management unit
44D: output control unit
44E: lesion detection unit
44F: initial information determination unit
45: recording medium
5: light source device
50: illumination lens
51: light source control unit
52: light source unit
53: light guide
60: air and water supply nozzle
IM: captured image data
P: object

What is claimed is:

1. An endoscope device, comprising:
an endoscope having an imaging element;
a sampling instrument configured to be inserted into the endoscope for sampling a living tissue, wherein the imaging element is configured to capture an image of the living tissue to generate a captured image data;
a control device that is electrically connected to the endoscope and supports an inspection using the living tissue sampled by the sampling instrument, the control device being configured to:
extract a feature amount from the captured image data;
perform an object recognition processing of recognizing whether or not the sampling instrument is included in the captured image data, using the feature amount;
recognize that the living tissue has been sampled by the sampling instrument based on a result of the object recognition processing; and
generate identification information corresponding to the living tissue when the living tissue is recognized to have been sampled; and
a display monitor that is electrically connected to the control device,
wherein the control device is configured to output the identification information and the captured image data associated with the identification information to the display monitor when the identification information is generated and cause the identification information and the captured image data associated with the identification information to be displayed on the display monitor.

2. The endoscope device according to claim 1,
wherein the control device is further configured to
record the identification information in association with the captured image data obtained in a period including a time point at which the living tissue corresponding to the identification information is recognized to have been sampled.

3. The endoscope device according to claim 2,
wherein the control device is configured to set the period as a period between the time point and a first time point before a first time from the time point.

4. The endoscope device according to claim 2,
wherein the control device is configured to set the period as a period between a second time point before a second time from the time point and a third time point after the time point.

5. The endoscope device according to claim 3,
wherein the control device is configured to
detect from the captured image data a site that is suspected by the control device to include a lesion, and
set a time point at which the site is first detected as the first time point.

6. The endoscope device according to claim 4
wherein the control device is configured to
detect from the captured image data a site that is suspected by the control device to include a lesion,
set a time point at which the site is first detected as the second time point, and sets at a time point at which the site is not detected as the third time point.

7. The endoscope device according to claim 4,
wherein the control device is configured to
detect from the captured image data a site that is suspected by the control device to include a lesion,
set a time point at which the site is first detected as the second time point, and set a time point at which a sampling mark generated by sampling the living tissue at the site by the sampling instrument is detected as the third time point.

8. The endoscope device according to claim 1,
wherein the endoscope device further includes a printer electrically connected to the control device and configured to print the identification information on a physical medium or a wireless tag writer electrically connected to the control device and configured to write the identification information to a wireless tag, and
wherein the control device is further configured to transmit the identification information to the printer or the wireless tag writer when the identification information is generated.

9. The endoscope device according to claim 1,
wherein the endoscope device further includes a printer electrically connected to the control device and configured to print the identification information on a physical medium or a wireless tag writer electrically connected to the control device and configured to write the identification information to a wireless tag, and wherein the control device is further configured to cause the identification information to be output from the printer or the wireless tag writer and cause the identification information and the captured image data associated with the identification information to be displayed on the display monitor.

10. The endoscope device according to claim 1, wherein the control device is further configured to recognize that the living tissue has been sampled when the control device determines from the result of the object recognition processing that the sampling instrument is included in the image captured by the imaging element.

11. The endoscope device according to claim 1, wherein the sampling instrument has a gripping part for gripping an object, and wherein the control device is further configured to recognize that the living tissue has been sampled when the control device determines from the result of the object recognition processing image information that the image captured by the imaging element shows the sampling instrument being in a state where the gripping part thereof is closed.

12. The endoscope device according to claim 1, wherein the sampling instrument has a gripping part for gripping an object, and wherein the control device is further configured to recognize that the living tissue has been sampled when the control device determines from the result of the object recognition processing that the image captured by the imaging element shows the object being gripped by the gripping part of the sampling element.

13. The endoscope device according to claim 1, wherein the identification information is one of a plurality of pieces of information lined up in a predetermined order, wherein the control device is configured to set any of the plurality of pieces of information as initial information which serves as a starting point, sequentially change the information to next information within the plurality of pieces for every time the living tissue is recognized to have been sampled, and generate the information being changed as the identification information, and determine the initial information based on the information input from a keyboard interface electrically connected to the control device and configured for inputting information.

14. The endoscope device according to claim 13, wherein the identification information is a number or an alphabet.

15. A biopsy support method of supporting an inspection using a living tissue sampled by a sampling instrument which is used by being inserted into an endoscope having an imaging element configured to capture an image of the living tissue to generate a captured image data, the biopsy support method comprising:

extracting, by using a control device, a feature amount from the captured image data;

performing, by using the control device, an object recognition processing of recognizing whether or not the sampling instrument is included in the captured image data, using the feature amount;

recognizing, by using the control device, that the living tissue has been sampled by the sampling instrument based on a result of the object recognition processing;

generating, by using the control device, identification information corresponding to the living tissue when the living tissue is recognized to have been sampled;

outputting, by using the control device, the identification information and the captured image data associated with the identification information to a display monitor when the identification information is generated; and causing, by using the control device, the identification information and the captured image data associated with the identification information to be displayed on the display monitor.

16. A non-transitory computer readable medium for storing a biopsy support program that supports an inspection using a living tissue sampled by a sampling instrument which is used by being inserted into an endoscope having an imaging element configured to capture an image of the living tissue to generate a captured image data, the biopsy support program causes a computer to execute a process comprising:

extracting a feature amount from the captured image data;

performing an object recognition processing of recognizing whether or not the sampling instrument is included in the captured image data, using the feature amount;

recognizing that the living tissue has been sampled by the sampling instrument based on a result of the object recognition processing;

generating identification information corresponding to the living tissue when the living tissue is recognized to has been sampled;

outputting the identification information and the captured image data associated with the identification information to a display monitor when the identification information is generated; and causing the identification information and the captured image data associated with the identification information to be displayed on the display monitor.

* * * * *